United States Patent [19]
Pritchett et al.

[11] Patent Number: 5,786,850
[45] Date of Patent: Jul. 28, 1998

US005786850A

[54] MULTIPLE ROOM PORTABLE CAMERA SYSTEM

[75] Inventors: James D. Pritchett, Dallas; Larry Gene Kaatz, Arlington; Boris Germanishkis, Richardson, all of Tex.

[73] Assignee: Ultrak, Inc., Carrollton, Tex.

[21] Appl. No.: 198,187

[22] Filed: Feb. 17, 1994

[51] Int. Cl.⁶ ............................................. H04N 7/18
[52] U.S. Cl. ........................ 348/158; 348/159; 348/705
[58] Field of Search ............................ 348/705, 706, 348/159, 158, 143, 77, 75, 74, 72, 71, 66, 65, 61; 345/1, 2; 340/825.51, 825.5, 825.17; H04N 7/18

[56] References Cited

U.S. PATENT DOCUMENTS

| | | | |
|---|---|---|---|
| 3,946,159 | 3/1976 | Fay | 340/182 |
| 4,037,250 | 7/1977 | McGahan et al. | 348/159 |
| 4,400,735 | 8/1983 | Strammello, Jr. | 358/181 |
| 4,947,245 | 8/1990 | Ogawa et al. | 348/66 |
| 4,977,449 | 12/1990 | Morgan | 348/159 |
| 5,065,343 | 11/1991 | Inoue | 345/1 |
| 5,124,789 | 6/1992 | Hiyama et al. | 348/74 |
| 5,214,421 | 5/1993 | Vernon et al. | 345/1 |
| 5,317,402 | 5/1994 | Wong et al. | 348/705 |
| 5,486,877 | 1/1996 | Tanaka | 348/705 |

*Primary Examiner*—Bryan S. Tung
*Attorney, Agent, or Firm*—Jenkens & Gilchrist, a Professional Corporation

[57] ABSTRACT

A multiple room portable camera system having a plurality of rooms, a camera unit, a switching unit, and a video printer. Each of the plurality of rooms has a monitor, a signal connector, and a control connector. The camera unit has a signal connector and a control connector for connecting to the signal connectors and control connectors in the plurality of rooms. The switching unit connects to each of the monitors, signal connectors, and control connectors of each of the rooms. Based on the connection of the control connector of the camera into the control connector of a particular room, the switching unit will route the camera signals from the camera, through the video printer, and return those signals only to the monitor of the room containing the camera.

19 Claims, 4 Drawing Sheets

FIG. 1

MULTIPLE ROOM PORTABLE CAMERA SYSTEM

BACKGROUND OF THE INVENTION

1. Field of the Invention

The present invention relates to a multiple room portable camera system, and more particularly, to a multiple room portable camera system providing images from the portable camera to monitors in particular rooms.

2. History of the Prior Art

Recent advances in electronics have decreased the size of the audio-visual equipment. This miniaturization of the equipment for audio-visual systems has lead to many new applications for the equipment. One example of a new application for audio-visual equipment is the use as an intra-oral camera. Intra-oral cameras enable a dentist or patient to view images of a patient's mouth on a video monitor. The intra-oral camera is placed within a patient's mouth and aimed at an object of interest. An image of the object of interest is transmitted from the intra-oral camera to a video monitor. The image can be carefully viewed on the monitor by both the dentist and the patient. Use of the intra-oral camera allows a dentist or physician to better provide an accurate prognosis, and also allows the patient to be better informed by the dentist or physician of a medical condition.

Although recent advances in electronics have allowed the miniaturization of audio-visual cameras for these varied applications, the cost for the equipment can still be quite high. Therefore, the dentist or physician may only have one camera for serving multiple operatories, or rooms. The camera must be moved from room to room for use with patients in different rooms.

A single camera that is moved from room to room must also be connected to a monitor for displaying the video image to the dentist or physician, and the patient. In one prior art system, a single monitor is connected to the camera, and both the camera and the monitor are moved from room to room. One disadvantage of moving the monitor between rooms with the camera is that monitors can be large and cumbersome to move. Another disadvantage to moving the monitor with the camera is that there may be a need for the monitor in one of the rooms without a camera, such as for showing video tapes.

Another prior art system overcomes the disadvantages of transporting a monitor with the camera from room to room by placing a monitor in each of the rooms. However, when using the camera with signal processing equipment, such as a video printer, the signal processing equipment must be moved from room to room with the camera, or there must be a signal processor in each room. Signal processors can be large and expensive, therefore to move the signal processor from room to room would be difficult because of the size, and risk damaging expensive equipment. Because the signal processor is only used with the camera, it would be a needless cost to have a signal processor in each room.

Yet another prior art system places monitors in each room, which are connected to an output of a signal processor, such as a video printer. A connector for the camera is located in each room and connected to the input of the video printer. This system allows the user to move a camera from room to room, and connect the camera to the connector in the room so that the monitor in the room will display images from the camera after they have been processed by the signal processor. However, a disadvantage to this method is that images from a camera connected in one room will be displayed on all monitors in all rooms. In many applications, when the camera is used in a particular room, it is desired to display the images from that camera only in that room which has the camera. As an example, when a dentist or physician uses a camera to display images of a patient, the patient's privacy requires that the images from the camera be displayed only in the room with the patient.

For the foregoing reasons, there is a need for a closed circuit camera and monitor system using one camera and one signal processing unit to service multiple rooms, each having a monitor, in a manner which provides private viewing of the images from the camera in only the room containing the camera.

SUMMARY OF THE INVENTION

To overcome the aforementioned short comings and deficiencies, the present invention generally provides a portable camera multiple site video system for utilizing a single portable video camera to take and display video pictures at a selected one of a plurality of picture sites comprising: a plurality of sites, each set comprising a video monitor, a site signal connector, and a site control connector; a portable video camera having a camera signal connector and a control site connector selectively connectable respectively to a selected site signal connector and site control connector; a video printer; a switching unit comprising a plurality of parallelly arranged site switches, one for each of said sites, said switches being wired to connect a given site signal connector to a video monitor for said site upon being thrown, and to connect said given site connector to said video printer upon being thrown; said switching unit further comprising a plurality of parallelly arranged relays, one associated with each of said site switches, said relays being wired to be actuated upon establishment of electrical connection between said camera signal control connector and a selected site control connector, to thereby throw a switch corresponding to said selected site control connector, and thus connect said site signal connector to the video monitor for that site, and to said video printer.

BRIEF DESCRIPTION OF THE DRAWINGS

For a more complete understanding of the present invention, and for further objectives and advantages thereof, reference may now be made to the following detailed description taken in conjunction with the accompanying drawings herein.

DETAILED DESCRIPTION

Figure 1:
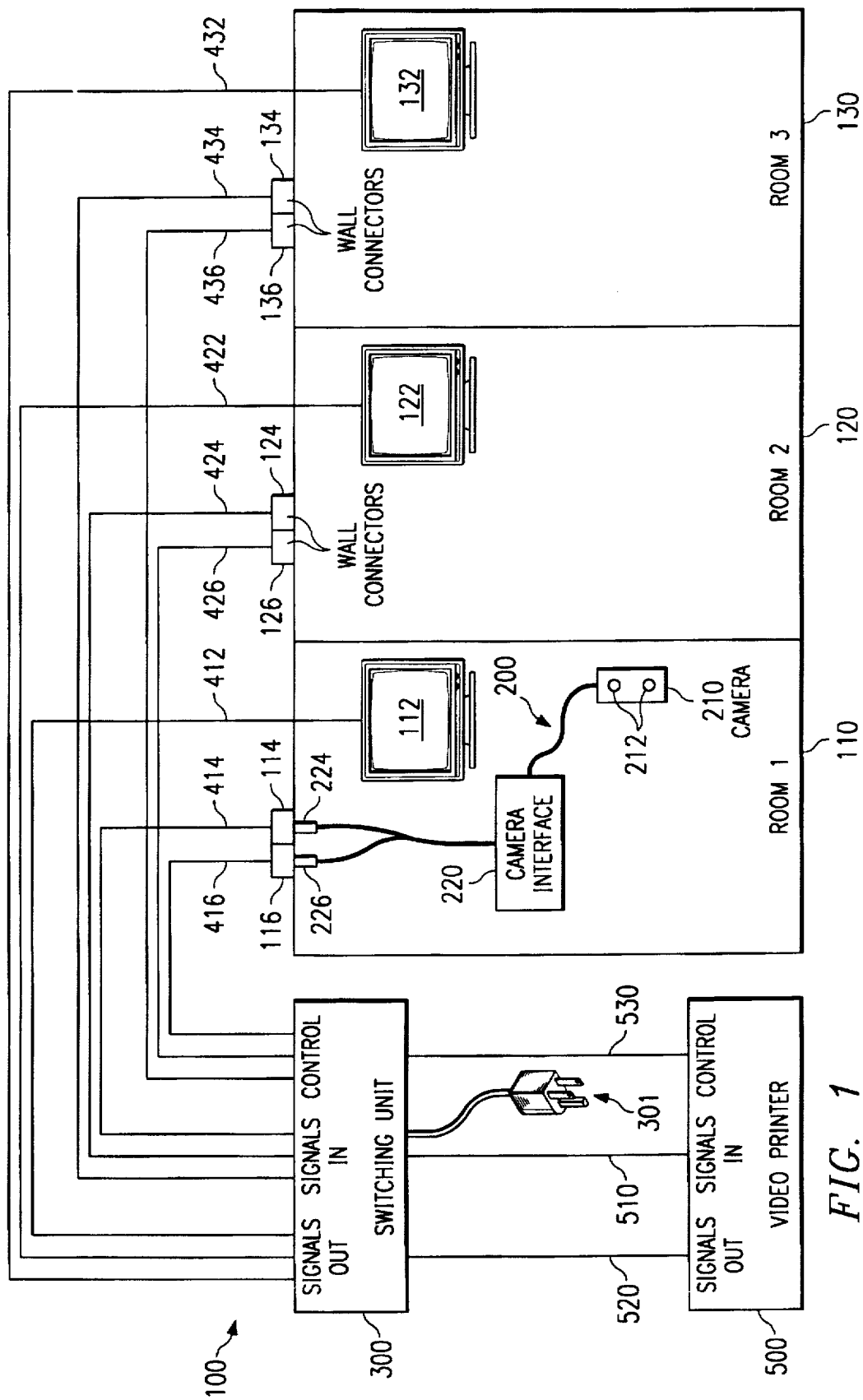
FIG. 1 shows a block diagram illustrating an embodiment of the present invention.

Referring now to the drawings, and more particularly to FIG. 1, there is shown an embodiment of the present invention illustrated as the multiple room portable camera system, indicated generally at 100. The camera system 100 generally comprises a plurality of rooms 110, 120, and 130, a camera unit indicated generally at 200, a switching unit 300, and a video printer 500. The camera unit 200 can be any type of video or audio-visual camera used for display on a monitor. The video printer can be any standard commercial video printer, such as the Sony™ Video Printer Model CVP-G700. Each room 110, 120, and 130, has a monitor 112, 122, and 132, a signal connector 114, 124, and 134, and a control connector 116, 126, and 136, respectively. The monitors 112, 122, and 132 can be any standard commercial monitor, such as the Panasonic™ Monitor Model CT 1383Y. The camera unit 200 has a camera 210 with a video printer control 212, which are connected to a camera interface 220. The camera interface 220 has a camera signal connector 224 and a camera control connector 226. The camera signal connector 224 and the camera control connector 226 are adapted to interface with the room signal connector 114, 124, or 134, and the room control connectors 116, 126, and 136, respectively.

Referring still to FIG. 1, the switching unit 300 has a power cord 301 for receiving power from an external source (not shown). The switching unit 300 is connected to the monitors 112, 122, and 132, by the monitor cables 412, 422, and 432, respectively. The room signal connectors 114, 124, and 134, are connected to the switching unit 300 by the camera signal cables 414, 424, and 434, respectively. The room control connectors 116, 126, and 136, are connected to the switching unit 300 by control cables 416, 426, and 436, respectively. The video printer 500 is connected to the switching unit 300 by a video printer cable 510, a video printer cable 520, and a control cable 530. However, the control cable 530 could also be connected to infrared emitters which control the video printer 500 through an infrared remote control receiver in the video printer 500.

Figure 2:
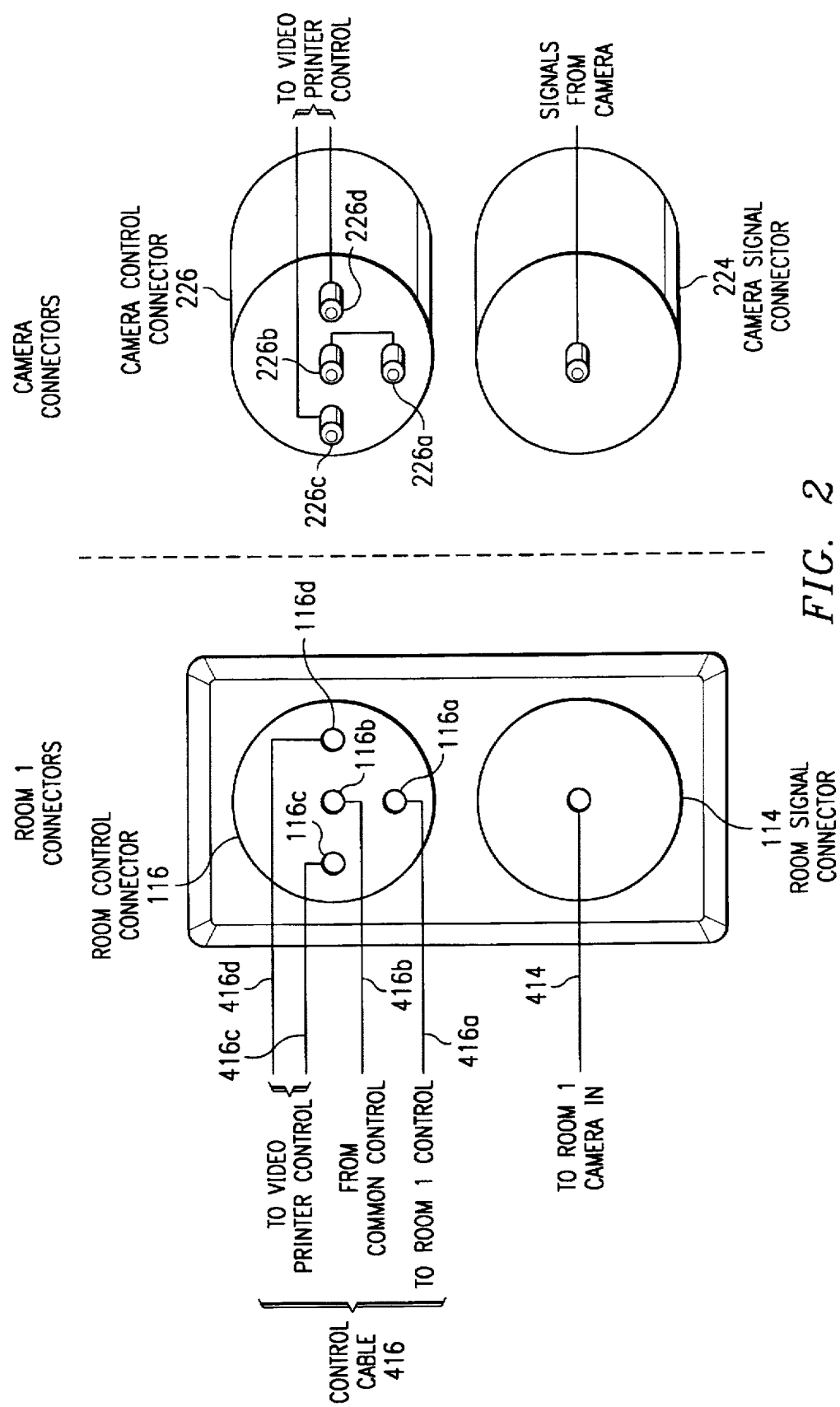
FIG. 2 shows an electrical schematic of the connection for the room wall connectors and the camera connectors of the embodiment illustrated in FIG. 1.

Referring now to FIG. 2, there is shown an electrical schematic of the room connectors and camera connectors of the embodiment illustrated in FIG. 1. The room connectors comprise a room signal connector 114 and a room control connector 116. The camera connectors comprise a camera signal connector 224 and a camera control connector 226.

Referring still to FIG. 2, the room signal connectors 114, 124, and 134, connect to the camera signal cables 414, 424, and 434, respectively. The room control connector 116 has four sockets 116a, 116b, 116c, and 116d. The sockets 116a, 116b, 116c, and 116d, connect to the room control line 416a, common control line 416b, video printer control line 416c, and video printer control line 416d, respectively. The lines 416a–d comprise lines in the control cable 416 as shown in FIG. 1. The room control connectors 424 and 426 have corresponding sockets which connect in the same manner to corresponding lines in the control cables 426 and 436, respectively.

Still referring to FIG. 2, the camera signal connector 224 receives signals from the camera unit 200. The camera control connector 226 has pins 226a, 226b, 226c, and 226d. A jumper electrically connects pin 226a with pin 226b. The pins 226c and 226d electrically connect to the printer controls 212 on the camera unit 200 shown in FIG. 1.

Still referring to FIG. 2, the camera signal connector 224 connects to one of the room signal connectors 114, 124, or 134 for transferring camera signals from the camera unit 200 to the camera signal cable 414, 424, or 434, respectively. When the camera control connector 226 is connected with the room control connector 116, the jumper in the camera control connector 226, closes a circuit between the common control line 416b and the room control line 416a connected to the room control connector 116. Also, connection of the room control connector 116 with the camera control connector 226 electrically connects the video printer control lines 416c and 416d to the video printer controls 212 on the camera unit 200. When the camera control connector 226 is connected with one the room control connectors 126 or 136, similar connections are made with the lines in the control cables 426 or 436, respectively.

Figure 3:
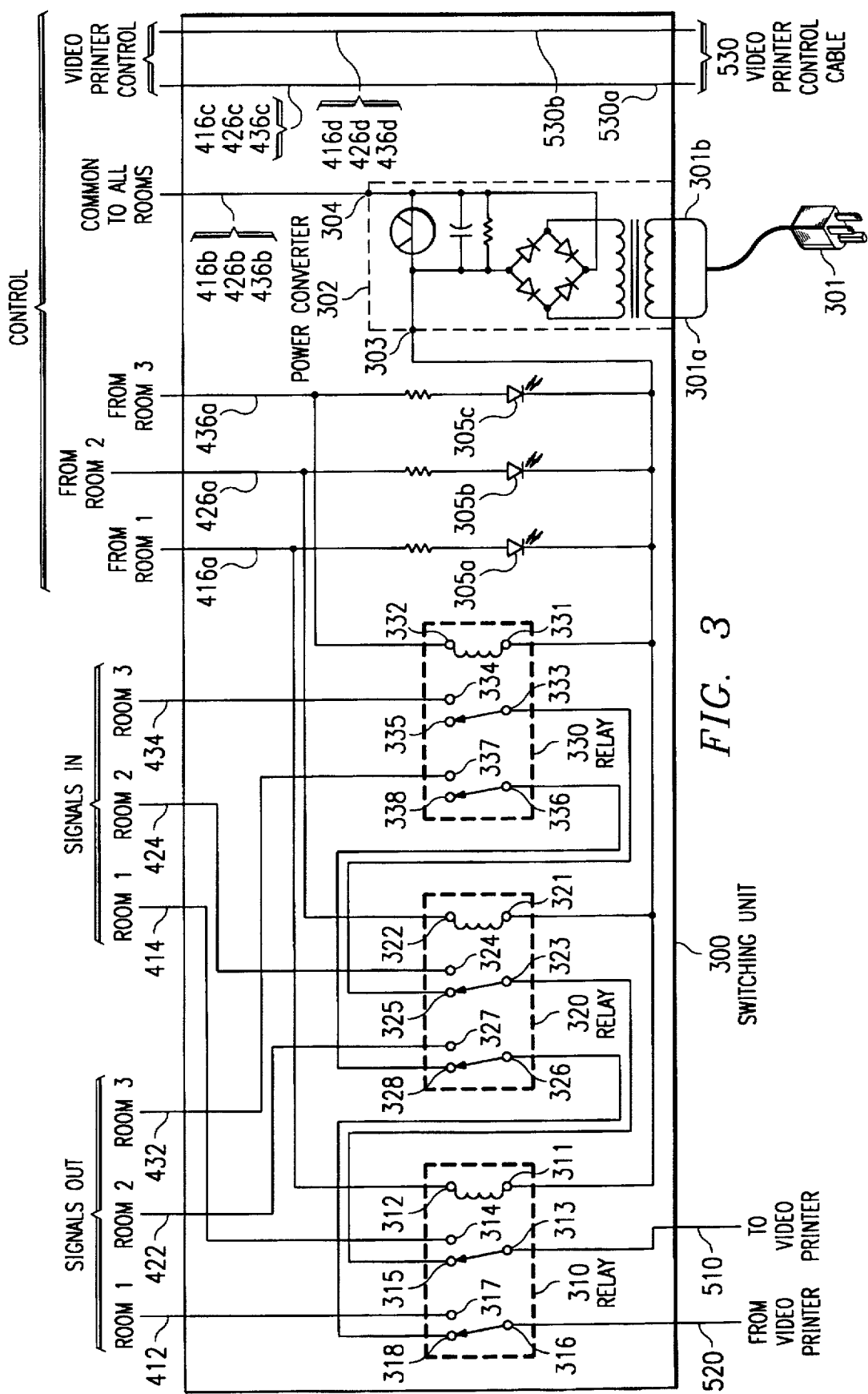
FIG. 3 shows an electrical schematic of a switching unit illustrated in the embodiment of FIG. 1.

Referring now to FIG. 3, there is shown an electrical schematic of the switching unit 300 from the embodiment of the present invention illustrated in FIG. 1. The switching unit 300 generally comprises a power cord 301, a power converter 302, and relays 310, 320, and 330. Although the power converter 302 is illustrated as being a component of the switching unit 300, the power converter 302 could be a separate unit or part of another unit in the system of the present invention.

Referring still to FIG. 3, the video printer control lines 416c, 426c, and 436c, are connected to the video control printer line 530a. The video control printer lines 416d, 426d, and 436d connect to the video printer control line 530b. The printer control lines 530a–b comprise lines in the printer control cable 530 as shown in FIG. 1

Still referring to FIG. 3, the relays, 310, 320, and 330, are double pole, double throw relays. Relay coil connections 311, 321, and 331, are all connected to a first power connection 303 of the power converter 302. A second power converter connection 304 connects to the common control lines 416b, 426b, and 436b. The second relay coil connections 312, 322, and 332, are connected to the room control lines 416a, 426a, and 436a, respectively. Light emitting diodes 305a, 305b, and 305c, connect between the room control lines 416a, 426a, and 436a, respectively, and the power connection 303 of the power converter 302.

Still referring to FIG. 3, the relay 310 has relay switch connections 313 and 316 which are electrically connected to video printer cables 510 and 520, respectively. Relay normally open (NO) terminals 314 and 317 are connected to the monitor cable 412 and the camera signal cable 414, respectively. Relay normally closed (NC) terminals 315 and 318 of the relay 310 are electrically connected to relay switch connections 323 and 326 of the relay 320, respectively. Relay NO terminals 324 and 327 of the relay 320 are connected to the camera signal cable 424 and the monitor cable 422, respectively. Relay NC terminals 325 and 328 of the relay 320 are electrically connected to the relay switch connections 333 and 336 of the relay 330, respectively. Relay NC terminals 334 and 337 of the relay 330 are electrically connected to the camera signal cable 434 and the monitor cable 332, respectively. Relay NC terminals 335 and 338 of the relay 330 are not electrically connected to any other component.

Still referring to FIG. 3, it can be seen how the relays 310, 320, and 330, of the switching unit 300 control which camera signal cable 414, 424, or 434 and monitor cable 412, 422, or 432, are electrically connected to the video printer cable 510 and 520, respectively. The relay switch connections 313 and 316 of the relay 310 are electrically connected to the video printer cables 510 and 520, respectively. Subsequent relay switch connections are electrically connected to the video printer cables 510 and 520 by electrically connecting to the respective relay NO terminals of the prior relay. For example, relay switch connections 323 and 326 are electrically connected to the video printer cables 510 and 520 by electrically connecting to the relay NC terminals 315 and 317 of the relay 310, respectively. This progression of electrically connecting relays to the video printer cables continues for each subsequent relay.

Still referring to FIG. 3, if none of the relays 310, 320, or 330 are activated, none of the camera signal cables 414, 424, or 434, or the monitor cables 412, 422, or 432 electrically connect to the relay switch connections of the relays 310, 320, or 330. However, when one of the relays 310, 320, or 330 is activated, the respective relay NO terminals of the activated relay are electrically connected to the relay switch connections of the activated relay, thereby electrically connecting the corresponding camera signal cable 414, 424, or 434 and the corresponding monitor cable 412, 422, or 432 to the respective video printer cables 510 and 520.

As an example, when relay 320 is activated, the camera signal cable 424, which is electrically connected to the relay No terminal 324, is electrically connected to the relay switch connection 323. Also, the monitor cable 422, which is electrically connected to the relay NO terminal 327, is electrically connected to the relay switch connection 326. Because the relay switch connections 323 and 326 are electrically connected through the relay 310 to the video printer cables 510 and 520, respectively, the camera signal cable 424 and the monitor cable 422 are electrically connected to the video printer cables 510 and 520, respectively.

Referring now to FIGS. 1, 2, and 3 in combination, the operation of the multiple room portable camera system 100 can be explained. The power converter 302 of the switching unit 300 converts power received from power cable 301 into a type of power which can be used in the relays 310, 320, or 330. Although the switching unit 300 illustrates the use of a power converter, a power converter would not be required in the present invention if the power source is in a form which can be used in the relays of the switching unit. This converted power is available at the first power connection 303 and the second power connection 304. Because the converted power is only used to activate the coils in the relays of the switching unit, the polarity of the power presented at 303 and 304 can be any direction, provided that the Light emitting diodes 305a, 305b, and 305c are connected to accommodate the polarity of the power converter 302.

Referring still to FIGS. 1, 2, and 3, in combination, the power from the power converter connection 303 is distributed to the relay coils at connections 311, 321, and 331. However, the power terminal connection 304 does not directly connect to the relay coils, but is connected to the common control lines 416b, 426b, and 436b. The lines 416b, 426b, and 436b, transfer power from the power converter connection 304 to the pins 116b, 126b, and 136b, respectively. If the camera control connector 226 is not connected to a room control connector 116, 126, or 136, the power from the power converter connection 304 does not complete a circuit to any other line.

Still referring to FIGS. 1, 2, and 3 in combination, when the camera control connector 226 is connected to one of the room control connectors 116, 126, or 136, the jumper from pin 226b to 226a in the camera control connector 226 completes a circuit between the particular common control line 416b, 426b, or 436b and the respective room control line 416a, 426a, or 436a. The power from the power converter connection 304 is then returned on the particular room control line 416a, 426a, or 436a to the respective relay coil connection 312, 322, or 332 in the switching unit 300. The power returning on one of the relay coil connections 312, 322, or 332, will activate the respective relay 310, 320, or 330.

Still referring to FIGS. 1, 2, and 3 in combination, the power returning on the particular room control line 416a, 426a, or 426a, will also illuminate the light emitting diode 305a, 305b, or 305c, connected between the power converter connection 303 and the particular room control line 416a, 426a, or 436a. The illuminated light emitting diode 305a, 305b, or 305c, will indicate which room 110, 120, or 130, respectively, has the camera unit 200 in use. The illuminated light emitting diodes 305a, 305b, and 305c, can also indicated if more than one camera unit is in use at one time, or where a problem might be located in the in the camera system 100.

Still referring to FIGS. 1, 2, and 3 in combination, when the camera control connector 226 is connected with a room control connector 116, 126, or 136, the respective relay 310, 320, or 330, is activated as described above. When a particular relay 310, 320, or 330, is activated, the camera signals from respective camera signal cables 414, 424, or 434, are sent through the video printer cable 510 to the video printer 500. Also, when a particular relay 310, 320, or 330 is activated, the respective monitor cable 412, 422, or 432 is electrically connected through the video printer cable 520 to the video printer 500. Because the camera unit 200 will not connected in any of the other rooms, the switching unit 300 will not send the camera signals from the camera unit 200 to the monitors in rooms where the camera is not located. In this manner the camera signals from the camera unit 200 are sent through the video printer 500 to only the monitor in the room containing the camera unit 200, thereby maintaining the patient's privacy.

As an example, if relay 310 is activated, the camera signal cable 414 is connected to the video printer 500 through the video printer line 510, and the video printer 500 is electrically connected to the monitor cable 412 through the video printer cable 520. Because the camera unit 200 is not connected in the other rooms 120 and 130, the switching unit 300 will not send the camera signals from the camera unit 200 to the monitors 122 and 132. In this manner the camera signals from the camera unit 200 are sent through the video printer 500 to only the monitor 112 in the room 110.

Figure 4:
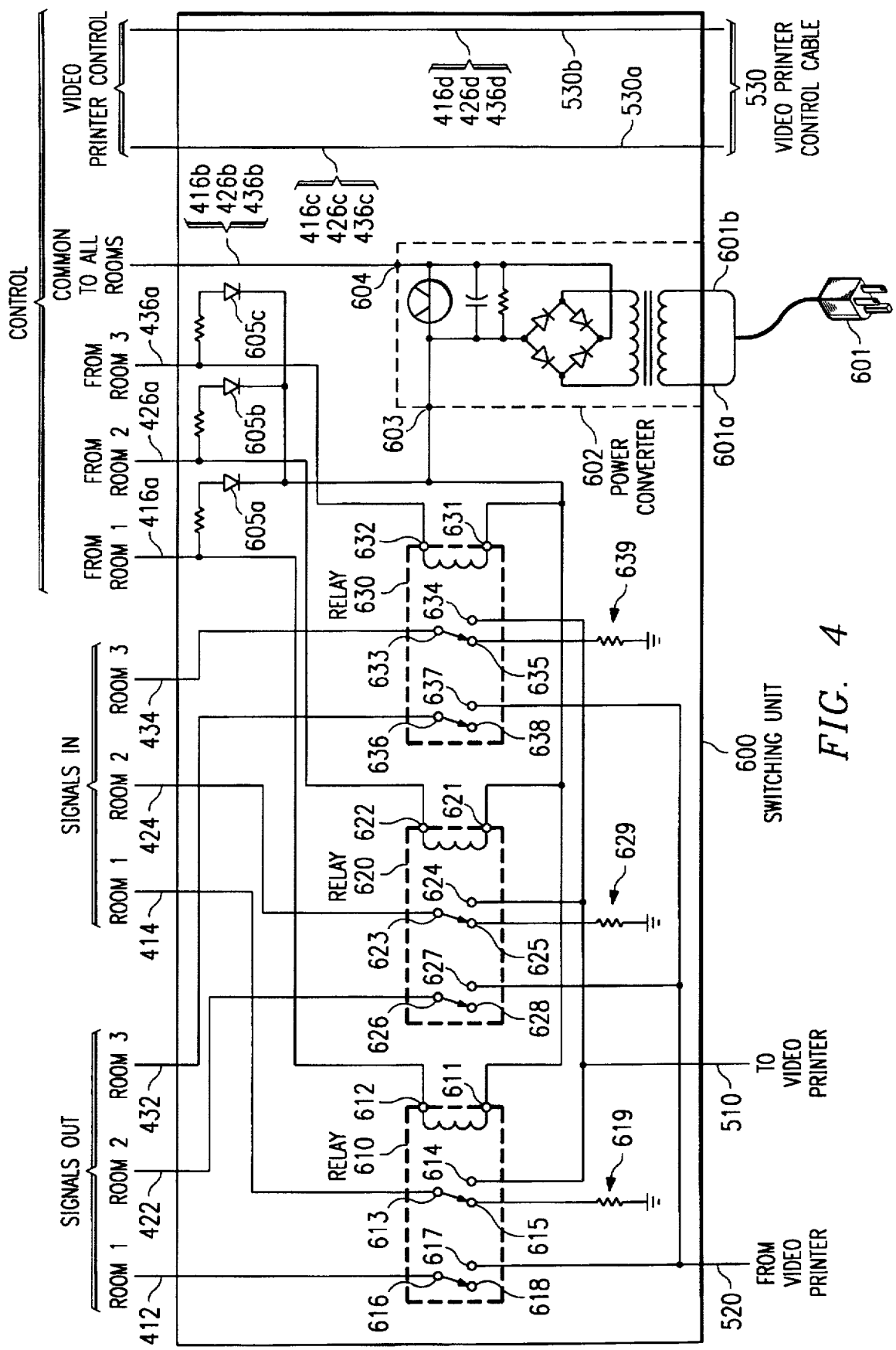
FIG. 4 shows an electrical schematic of a switching unit for an alternate embodiment of the present invention.

Referring now to FIG. 4, there is shown an electrical schematic of a switching unit 600 to be used in place of the switching unit in FIG. 1, for an alternate embodiment of the present invention illustrated in FIG. 1. The switching unit 600 generally comprises a power cord 601, a power converter 602, and relays 610, 620, and 630. Although the power converter 602 is illustrated as being a component of the switching unit 600, the power converter 602 could be a separate unit or part of another unit in the system of the present invention.

Referring still to FIG. 4, the video printer control lines 416c, 426c, and 436c, are connected to the video control printer line 530a. The video control printer lines 416d, 426d, and 436d connect to the video printer control line 530b. The printer control lines 530a-b comprise lines in the printer control cable 530 as shown in FIG. 1

Still referring to FIG. 4, the relays, 610, 620, and 630, are double pole, double throw relays. Relay coil connections 611, 621, and 631, are all connected to a first power connection 603 of the power converter 602. A second power converter connection 604 connects to the common control lines 416b, 426b, and 436b. The second relay coil connections 612, 622, and 632, are connected to the room control lines 416a, 426a, and 436a, respectively. Light emitting diodes 605a, 605b, and 605c, connect between the room control lines 416a, 426a, and 436a, respectively, and the power connection 603 of the power converter 602.

Referring still to FIG. 4, the relay switch connections 613, 623, and 636 are connected to the camera signal cables 414, 424, and 434, respectively. The relay NC terminals 615, 625, and 635, are connected to the grounded loads 619, 629, and 639, respectively. The relay NO terminals 614, 624, and 634, are connected to the video printer cable 510. The relay switch connections 616, 626, and 636 are connected to the monitor signal cables 412, 422, and 432, respectively. The relay No terminals 617, 627, and 637 are connected to the video printer cable 520. Alternatively, the relay switch connections 616, 626, and 636 are connected to the video printer cable 520, and the relay NO terminals 617, 627, and 637 are connected to the monitor signal cables 412, 422, and 432, respectively.

Still referring to FIG. 4, when the relays 610, 620, or 630, are not activated the relay NO terminals 617, 626, or 636 do not connect with the relay switch contacts 616, 626, and 636, and therefore no signal is transmitted from the video printer cable 520 to the monitor cables 412, 422, or 432. Also when the relays 610, 620, or 630 are not activated, the relay switch contacts 613, 623, or 636 are electrically connected to the relay NC terminals 615, 625, or 635, respectively, thereby connecting the camera signal cable 414, 424, or 426 to the grounded resistor loads 619, 629, or 639, respectively. In this manner, if the camera signal connector 224 is connected to one of the room signal connectors 114, 124, or 134, the camera signals will be grounded through a grounded load 619, 629, or 639.

Still referring to FIG. 4, when one of the relays 610, 620, or 630 is activated, the relay NO terminals 617, 626, or 636 electrically connect with the relay switch contacts 616, 626, and 636, thereby electrically connecting the video printer cable 520 to the monitor cables 412, 422, or 432. Also when one of the relays 610, 620, or 630 is activated, the relay switch contacts 613, 623, or 636 are electrically connected to the relay NO terminals 615, 625, or 635, respectively, thereby connecting the camera signal cable 414, 424, or 426 to the monitor cable 510.

Referring now to FIGS. 1, 2, and 4 in combination, the operation of the multiple room portable camera system 100 can be explained. The power converter 602 of the switching unit 600 converts power received from power cable 601 into a type of power which can be used in the relays 610, 620, or 630. Although the switching unit 600 illustrates the use of a power converter, a power converter would not be required in the present invention if the power source is in a form which can be used in the relays of the switching unit. This converted power is available at the first power connection 603 and the second power connection 604. Because the converted power is only used to activate the coils in the relays of the switching unit, the polarity of the power presented at 603 and 604 can be any direction, provided that the light emitting diodes 605a, 605b, and 605c are connected to accommodate the polarity of the power converter 602.

Referring still to FIGS. 1, 2, and 4, in combination, the power from the power converter connection 603 is distributed to the relay coils at connections 611, 621, and 631. However, the power terminal connection 604 does not directly connect to the relay coils, but is connected to the common control lines 416b, 426b, and 436b. The lines 416b, 426b, and 436b, transfer power from the power converter connection 604 to the pins 116b, 126b, and 136b, respectively. If the camera control connector 226 is not connected to a room control connector 116, 126, or 136, the power from the power converter connection 604 does not complete a circuit to any other line.

Still referring to FIGS. 1, 2, and 4 in combination, when the camera control connector 226 is connected to one of the room control connectors 116, 126, or 136, the jumper from pin 226b to 226a in the camera control connector 226 completes a circuit between the particular common control line 416b, 426b, or 436b and the respective room control line 416a, 426a, or 436a. The power from the power converter connection 604 is then returned on the particular room control line 416a, 426a, or 436a to the respective relay coil connection 612, 622, or 632 in the switching unit 600. The power returning on one of the relay coil connections 612, 622, or 632, will activate the respective relay 610, 620, or 630.

Still referring to FIGS. 1, 2, and 4 in combination, the power returning on the particular room control line 416a, 426a, or 426a, will also illuminate the light emitting diode 605a, 605b, or 605c, connected between the power converter connection 603 and the particular room control line 416a, 426a, or 436a. The illuminated light emitting diode 605a, 605b, or 605c, will indicate which room 110, 120, or 130, respectively, has the camera unit 200 in use. The illuminated light emitting diodes 605a, 605b, and 605c, can also indicated if more than one camera unit is in use at one time, or where a problem might be located in the in the camera system 100.

Still referring to FIGS. 1, 2, and 4 in combination, when the camera control connector 226 is connected with a room control connector 116, 126, or 136, the respective relay 610, 620, or 630, is activated as described above. When a particular relay 610, 620, or 630, is activated, the camera signals from respective camera signal cables 414, 424, or 434, are sent through the video printer cable 510 to the video printer 500. Also, when a particular relay 610, 620, or 630 is activated, the respective monitor cable 412, 422, or 432 is electrically connected through the video printer cable 520 to the video printer 500. Because the camera unit 200 will not connected in any of the other rooms, the switching unit 600 will not send the camera signals from the camera unit 200 to the monitors in rooms where the camera is not located. In this manner the camera signals from the camera unit 200 are sent through the video printer 500 to only the monitor in the room containing the camera unit 200, thereby maintaining the patient's privacy.

Referring now to FIGS. 1, 2, 3, and 4, it can be seen that privacy of a patient's image created by camera 200 is maintained in the present invention by sending the signals from the camera unit 200 to the video printer 500 and back to only the monitor in the particular room with the patient. The prior art, however, sent the video signals from the camera to the monitors in all rooms, thereby compromising the patient's privacy. Discovery of this problem in the prior art, and the solution thereof is a part of the present invention. The camera unit 200 can control the video printer 500 by passing the video printer controls through the particular control cable for the room to the switching unit 300 or 600, and from the switching unit 300 or 600, over the control line 530 to the video printer 500. Rooms which do not have the camera unit 200 connected to the wall switches therein, will not return control power to the switching unit 300 or 600, for activating relays. Therefore, the relays in the switching unit 300 or 600, corresponding to rooms without the camera unit 200, will not activate, and therefore no connection is made between the output of the video printer 500 and the monitor of the particular room. In this manner, the video image of a patient created by the camera unit 200 is processed by the video printer 500, but is only displayed on the monitor in the room with the patient. Although FIG. 1 illustrates the use of three rooms, any number of rooms over two could be used with the present invention by altering the number of relays in the switching unit to match the number of rooms.

It is thus believed that the operation and construction of the present invention will be apparent from the foregoing description. While the method, apparatus, and system shown and described herein is characterized as being a preferred embodiment, it will be readily apparent that various changes and modifications could be made therein without departing from the spirit and scope of the invention as defined in the following claims. For example, the room control lines 416a, 426a, and 436a and the common control lines 416b, 426b, and 436b can be connected to switches in the rooms 110, 120, and 130, as and alternate to using the jumper between pins 226a and 226b in the camera control connector 226.

What is claimed is:

1. A portable camera multiple site video system for utilizing a single portable video camera to take and display video pictures at a selected one of a plurality of picture sites comprising:

a plurality of sites, each site comprising a video monitor, a site signal connector, and a site control connector;

a portable video camera having a camera signal connector and a camera control connector selectively connectable respectively to the site signal connectors and the site control connectors of said sites;

a video printer;

a switching unit comprising a plurality of site switches, each one of the site switches corresponding with a different one of said sites, each one of the site switches being wired to electrically connect the site signal connector of the corresponding site to the video monitor of the corresponding site upon being thrown, and to electrically connect the site signal connector of the corresponding site to said video printer upon being thrown;

said switching unit further comprising a plurality of relays, each one of the relays being associated with a different one of the site switches, each one of the relays being wired to be actuated upon establishment of an electrical connection between the camera control connector and the site control connector of the corresponding site for the associated site switch, and wherein activation of one of the relays throws the associated site switch, thereby electrically connecting the site signal connector of the corresponding site to the video monitor of the corresponding site, and to said video printer.

2. The system according to claim 1, further comprising a plurality of means for indicating actuation of the relays, one of said means for indicating associated with each of said relays, wherein actuation of one of said relays causes the associated means for indicating to indicate that the associated relay has been activated.

3. The system according to claim 2, wherein said means for indicating illuminates upon actuation of the associated one of said relays.

4. The system according to claim 1, further comprising:

each one of the site switches of said switching unit including a double pole double throw switch each having a first switch with a first switching element, a first normally open terminal, and first normally closed terminal, and a second switch with a second switching element, a second normally closed terminal, and a second normally open terminal;

the first switching element of the a first one of the site switches being electrically connected to an output of said video printer, and the second switching element of the first one of the site switches being electrically connected to an input of said video printer;

the first switching element of a second one of the site switches being electrically connected to the first normally closed terminal of the first one of the site switches, and the second switching element of the second one of the site switches being electrically connected to the second normally closed terminal of the first one of the site switches;

the site signal connector for a first one of said plurality of sites being electrically connected to the second normally open terminal of the first one of the site switches, and the site signal connector for a second one of said plurality of sites being electrically connected to the second normally open terminal of the second one of the site switches; and the video monitor in the first one of said plurality of sites being electrically connected to the first normally open terminal of the first one of the site switches, and the video monitor in the second one of said plurality of sites being electrically connected to the first normally open terminal of the second one of the site switches.

5. The system according to claim 4, further comprising a plurality of means for indicating actuation of the relays, one of said means for indicating associated with each of said relays, wherein actuation of one of said relays causes the associated means for indicating to indicate that the associated relay has been activated.

6. The system according to claim 4, including a power supply having a first side electrical connection and a second side electrical connection; wherein each one of the plurality of relays include electrical coils having a first end and a second end, the first end of the coils for all of the plurality of site switches being electrically connected to the first side electrical connection of said power supply; wherein the site control connectors of said plurality of sites each include a first control site connection and a second site control connection, the first site control connections of the site control connectors for all of said plurality of sites being electrically connected to the second side electrical connection of said power supply, the second site control connection of the site control connector in each of said plurality of sites being electrically connected to the second end of the coils for the relays associated with the corresponding site switches in said switching unit; and wherein the control site connector of said portable video camera includes a first camera control connection and a second camera control connection for electrically connecting with the first site control connection and the second site control connections, respectively, in the site control connectors of said plurality of sites, the first camera control connection and the second camera control connection of said portable video camera being electrically connected.

7. The system according to claim 6, wherein said power supply is a power converter supplying DC power from an AC power source.

8. The system according to claim 7, further comprising a plurality of means for indicating activation of the relays, one of said means for indicating associated with each of said relays, wherein electrical connection of the coil of one of said relays with the power supply causes an associated means for indicating to indicate that the associated relay has been activated.

9. The system according to claim 8, wherein said plurality of means f Or indicating are light emitting diodes having a first electrical connection and a second electrical connection, and wherein the first electrical connection and the second electrical connection for each of said light emitting diodes is electrically connected to the first end and the second end of the coils, respectively, of each associated relay.

10. The system according to claim 4, wherein said portable video camera includes a printer control switch being electrically connected to a printer control connection in the camera control connector of said portable video camera; wherein each of the site control connectors in said plurality of sites include printer control connections for electrical connection with the printer control connection in the camera control connector of said portable video camera; and wherein each of the printer control connections in the site control connector of said plurality of sites are electrically connected to a control input of said video printer.

11. A portable camera multiple site video system for utilizing a single portable video camera to take and display video pictures at a selected one of a plurality of picture sites comprising:

a plurality of sites, each site comprising a video monitor, a site signal connector, and a site control connector;

a portable video camera having a camera signal connector and a camera control connector selectively connectable respectively to the site signal connectors and the site control connectors of said sites;

a video printer;

a switching unit comprising a plurality of site switches, each one of the site switches corresponding with a different one of said sites, each one of the site switches being wired to electrically connect the site signal connector of the corresponding site to the video monitor of the corresponding site upon being thrown, and to electrically connect the site signal connector of the corresponding site to said video printer upon being thrown;

said switching unit further comprising a plurality of relays, each one of the relays being associated with a different one of the site switches, each one of the relays being wired to be actuated upon establishment of an electrical connection between the camera control connector and the site control connector of the corresponding site for the associated site switch, and wherein activation of one of the relays throws the associated site switch, thereby electrically connecting the site signal connector of the corresponding site to the video monitor of the corresponding site, and to said video printer;

each one of the site switches of said switching unit including a double pole double throw switch each having a first switch with a first switching element, a first normally open terminal, and first normally closed terminal, and a second switch with a second switching element, a second normally closed terminal, and a second normally open terminal;

the first switching element of a first one of the site switches being electrically connected to an output of said video printer, and the second switching element of the first one of the site switches being electrically connected to an input of said video printer;

the first switching element of a second one of the site switches being electrically connected to the first normally closed terminal of the first one of the site switches, and the second switching element of the second one of the site switches being electrically connected to the second normally closed terminal of the first one of the site switches;

the site signal connector for a first one of said plurality of sites being electrically connected to the second normally open terminal of the first one of the site switches and the site signal connector for a second one of said plurality of sites being electrically connected to the second normally open terminal of the second one of the site switches;

the video monitor in the first one of said plurality of sites being electrically connected to the first normally open terminal of the first one of the site switches, and the video monitor in the second one of said plurality of sites being electrically connected to the first normally open terminal of the second one of the site switches; and wherein said portable video camera includes a printer control switch being electrically connected to a printer control connection in the camera control connector of said portable video camera; wherein each of the site control connectors in said plurality of sites include printer control connections for electrical connection with said printer control connection in the camera control connector of said portable video camera; and wherein each of said printer control connections in said site control connector of said plurality of sites are electrically connected to an infrared emitter; and wherein said video printer includes an infrared remote control receiver for receiving the signals from said infrared emitter.

12. The system according to claim 1, further comprising:

each one of the site switches of said switching unit including a double pole double throw switch each having a first switch with a first switching element, a first normally open terminal, and a first normally closed terminal, and a second switch with a second switching element, a second normally closed terminal, and a second normally open terminal;

the video monitor of a first one of said plurality of sites being electrically connected to the first switching element of a first one of the site switches, and the video monitor of a second one of said plurality of sites being electrically connected to the first switching element of a second one of the site switches;

the site signal connector of the first one of said plurality of sites being electrically connected to the second switching element of the first one of the site switches, and the site signal connector of the second one of said plurality of sites being electrically connected to the second switching element of the second one of the site switches;

the first normally open terminal of the first one of the site switches being electrically connected to an output of said video printer, and the first normally open terminal of the second one of the site switches being electrically connected to the output of said video printer; and the second normally open terminal of the first one of the site switches being electrically connected to an input of said video printer, and the second normally open terminal of the second one of the site switches being electrically connected to the input of said video printer.

13. The system according to claim 12, further comprising a plurality of means for indicating actuation of the relays, one of said means for indicating associated with each of said relays, wherein actuation of one of said relays causes the associated means for indicating to indicate that the associated relay has been activated.

14. The system according to claim 12, including a power supply having a first side electrical connection and a second side electrical connection; wherein each one of the plurality of relays include electrical coils having a first end and a second end, the first end of the coils for all of the plurality of site switches being electrically connected to the first side electrical connection of said power supply; wherein the site control connectors of said plurality of sites each include a first site control connection and a second site control connection, the first site control connections of the site control connectors for all of said plurality of sites being electrically connected to the second side electrical connection of said power supply, the second site control connection of the site control connector in each of said plurality of sites being electrically connected to the second end of the coils for the relays associated with the corresponding site switches in said switching unit; and wherein the camera control connector of said portable video camera includes a first camera control connection and a second camera control connection for electrically connecting with the first site control connection and the second site control connections, respectively, in the site control connectors of said plurality of sites, the first camera control connection and the second camera control connection of said portable video camera being electrically connected.

15. The system according to claim 14, wherein said power supply is a power converter supplying DC power from an AC power source.

16. The system according to claim 14, further comprising a plurality of means for indicating activation of the relays, one of said means for indicating associated with each of said relays, wherein electrical connection of the coil of one of said relays with power supply causes an associated means for indicating to indicate that the associated relay has been activated.

17. The system according to claim 16, wherein said plurality of means for indicating are light emitting diodes having a first electrical connection and a second electrical connection, and wherein the first electrical connection and the second electrical connection for each of said light emitting diodes is electrically connected to the first end and the second end of the coils, respectively, of each associated relay.

18. The system according to claim 12, wherein said portable video camera includes a printer control switch being electrically connected to a printer control connection in the camera control connector of said portable video camera; wherein each of the site control connectors in said plurality of sites include printer control connections for electrical connection with the printer control connection in the camera control connector of said portable video camera; and wherein each of the printer control connections in the site control connector of said plurality of sites are electrically connected to a control input of said video printer.

19. A portable camera multiple site video system for utilizing a single portable video camera to take and display video pictures at a selected one of a plurality of picture sites comprising:

a plurality of sites, each site comprising a video monitor, a site signal connector, and a site control connector;

a portable video camera having a camera signal connector and a camera control connector selectively connectable respectively to the site signal connectors and the site control connectors of said sites;

a video printer;

a switching unit comprising a plurality of site switches, each one of the site switches corresponding with a different one of said sites, each one of the site switches being wired to electrically connect the site signal connector of the corresponding site to the video monitor of the corresponding site upon being thrown, and to electrically connect the site signal connector of the corresponding site to said video printer upon being thrown;

said switching unit further comprising a plurality of relays, each one of the relays being associated with a different one of the site switches, each one of the relays being wired to be actuated upon establishment of an electrical connection between the camera control connector and the site control connector of the corresponding site for the associated site switch, and wherein activation of one of the relays throws the associated site switch, thereby electrically connecting the site signal connector of the corresponding site to the video monitor of the corresponding site, and to said video printer;

each one of the site switches of said switching unit including a double pole double throw switch each having a first switch with a first switching element, a first normally open terminal, and a first normally closed terminal, and a second switch with a second switching element, a second normally closed terminal, and a second normally open terminal;

the video monitor of a first one of said plurality of sites being electrically connected to the first switching element of a first one of the site switches, and the video monitor of a second one of said plurality of sites being electrically connected to the first switching element of a second one of the site switches;

the site signal connector of the first one of said plurality of sites being electrically connected to the second switching element of the first one of the site switches, and the site signal connector of the second one of said plurality of sites being electrically connected to the second switching element of the second one of the site switches;

the first normally open terminal of the first one of the site switches being electrically connected to an output of said video printer, and the first normally open terminal of the second one of the site switches being electrically connected to the output of said video printer;

the second normally open terminal of the first one of the site switches being electrically connected to an input of said video printer, and the second normally open terminal of the second one of the site switches being electrically connected to the input of said video printer; and wherein said portable video camera includes a printer control switch being electrically connected to a printer control connection in the camera control connector of said portable video camera; wherein each of the site control connectors in said plurality of sites include printer control connections for electrical connection with said printer control connection in the camera control connector of said portable video camera; and wherein each of the printer control connections in said site control connector of said plurality of sites are electrically connected to an infrared emitter; and wherein said video printer includes an infrared remote control receiver for receiving the signals from said infrared emitter.

* * * * *